United States Patent

Risse

Patent Number: 5,588,833
Date of Patent: Dec. 31, 1996

[54] SYSTEM OF TREATMENT FOR USE IN FUNCTIONAL ORTHODONTICS

[76] Inventor: Georg Risse, Bogenstrasse 15-16, D-4400 Münster, Germany

[21] Appl. No.: 340,645

[22] Filed: Nov. 16, 1994

Related U.S. Application Data

[63] Continuation of Ser. No. 965,408, Feb. 23, 1993, abandoned.

[51] Int. Cl.⁶ ........................................ A61C 3/00
[52] U.S. Cl. ........................ 433/24; 433/8; 433/20
[58] Field of Search ........................... 433/8, 9, 10, 11, 433/12, 13, 14, 15, 16, 17, 20, 24

[56] References Cited

U.S. PATENT DOCUMENTS

| | | |
|---|---|---|
| 2,379,011 | 6/1945 | Laskin . |
| 3,302,288 | 2/1967 | Tepper . |
| 3,526,961 | 9/1970 | Kesling . |
| 4,037,324 | 7/1977 | Andreasen . |
| 4,186,487 | 2/1980 | Wallshein . |
| 4,249,897 | 2/1981 | Anderson . |
| 4,585,414 | 4/1986 | Kottemann . |
| 4,659,310 | 4/1987 | Kottemann . |
| 4,676,746 | 6/1987 | Klapper . |
| 4,793,804 | 12/1988 | Schudy . |
| 4,818,226 | 4/1989 | Berendt et al. . |

OTHER PUBLICATIONS

Unitek Catalog, "HI-T The Livelier Wire That Works Over a Greater Distance", vol. 49, No. 12, p. 8. Dec., 1963.

*Primary Examiner*—Nicholas D. Lucchesi
*Attorney, Agent, or Firm*—Knobbe, Martens, Olson & Bear

[57] ABSTRACT

The invention relates to rectangular wires and brackets for use in orthodontic treatment methods as well as to a system of treatment comprising these wires and brackets. The wires according to the invention have a smaller cross-section than conventional wires, and the cross-section of the slots of the brackets is also smaller than in conventional systems and can be so adjusted to the cross-section of the wires that the wires have sufficient play in the slots so as to allow selective three-dimensional tooth movement with biologically acceptable forces. The invention also relates to orthodontic methods using such wires and brackets.

16 Claims, No Drawings

SYSTEM OF TREATMENT FOR USE IN FUNCTIONAL ORTHODONTICS

This application is a continuation of application Ser. No. 07/965,408, filed Feb. 23, 1993, now abandoned.

TECHNICAL FIELD OF THE INVENTION

The invention relates to a rectangular wire for use as archwire in orthodontics and to a bracket or band for use in orthodontics. The invention also relates to a system of treatment comprising such archwires and brackets or bands, and to an orthodontic method.

BACKGROUND OF THE INVENTION

The treatment of the position of the teeth and the treatment of the position of the upper and lower jaw is generally possible by orthopedic and orthodontic means.

The orthopedic treatment or functional orthopedics has mainly been used in Europe. The appliances used in orthopedics are removable. They therefore produce forces on the teeth mainly intermittently and react as growth stimulators intermaxillary and intramaxillary. The exact positioning of teeth is, however, not possible because there are only point contacts between appliances and teeth.

The orthodontic treatment is characterized by its fixed appliances. The forces applied by fixed appliances react on the teeth in all three dimensions at the same time. The position of the upper jaw and its teeth in relation to the lower jaw and its teeth is handled by additional intermaxillar and extraoral appliances, like elastics and headgear or facebow. In stimulating growth and growth direction of jaws, muscles, habits and teeth, fixed appliances seem to be in different situations less effective than removable appliances, but are highly superior in the detailed positioning of teeth in their special function.

The vast majority of all cases represents a combination of growth problems, like position of the jaws, and wrong positioned teeth in the upper and lower jaw. Therefore a combined therapy with both appliances, using primarily removable appliances and in particular for dental anomalies with rest growth problems fixed appliances, is indicated.

Historically functional orthopedics in its narrow sense has been developed in Europe and comprises essentially removable appliances only, whereas orthodontics has been predominantly developed in the U.S.A. and comprises mainly fixed appliances.

Functional orthopedics with its removable appliances works mostly with inductive, so-called functional forces with functional reaction on bones, teeth, muscles, parodontium and growth centers, whereas the orthodontic treatment with its fixed appliances usually influences biological structures mechanically.

The fixed appliances consist mainly of two basic units. The one part, namely the bracket or band, is firmly fixed on each tooth and contains a slot with a specific cross-section. The other part, namely the archwire, is fixed into the slot and combines all teeth of a jaw. The bands originally consisted of metal rings onto which attachments with slots were welded. Brackets are essentially only these attachments without the band or ring, and are directly fixed on each tooth by adhesive materials.

By using a rectangular slot in the brackets, which are fixed on the teeth with a fixed rectangular wire in the rectangular slot, the effect of the force is acting three-dimensionally. The individual teeth can be influenced in their height, in their angulation, and in their axial inclination.

The brackets have to be placed extremely accurately in height and angulation to prevent unwanted extrusions or angulations of the different teeth when a straight wire is ligated. The third dimension providing a torque acting on a tooth is applied differently in the different techniques. The displacement of the axial inclination of a tooth can either be provided by a torsion in the wire or, if straight wires are used, by an adequate inclination of the slot in the bracket.

The different techniques in orthodontics differ mainly in different angalations and torques in the slots of the brackets. When using a straight wire without torsion, the final axial position of the tooth is essentially predetermined by the angular position of the slot in the bracket. The most famous techniques are the "Jaraback", "Rickets", "Alexander", "Hilgers", and "Roth", Technique. A survey of the different techniques is to be found for example in the handbook "Handbuch für die kieferorthopädische Praxis, Band II, des Berufsverbandes Deutscher Kieferorthopäden 1988".

All these orthodontic techniques have in common both a rectangular slot and a rectangular archwire. With the exception of the Roth technique, a slot of 0.018×0.022 inches is used, and rectangular wires having a size of 0,016×0.016, 0,016×0.022, 0,017×0.022 and 0.018×0.022 inches. In the Roth technique, a slot with a size of 0,022×0.025 inches and archwires up to this size are used. Note that all commercial archwire cross-sections are given in inch or 1/1000 inch; 1 inch=25.4 mm.

To reduce the enormous forces from one tooth to the other, there were used so-called multiloop arches particularly in the initial levelling phase of the Jaraback technique. In putting more wire, namely a loop, inbetween the distance from one tooth to another the amount of force can be reduced. The disadvantages of this multiloop technique are the following: It is extremely difficult to bend a wire, to activate the wire, and to control the forces on the teeth and their movement, and it takes a great deal of time to obtain its shape, which a patient often will not accept. Additionally these loops may injure the soft tissue directly, and tooth brushing is hardly possible with the consequence of following damage to the teeth by various decalcifications and inflammations of the soft tissues of the parodontium.

In order to avoid all these disadvantages different and more elastic wires made of new alloys were developed in order to allow the handling of the teeth with straight wires which are not broken by a loop. The problem to avoid the high forces has been tried to be solved by higher elasticity and lower stiffness of the alloys.

However, the main problem in handling these wires is, surprisingly, their elasticity, because it is more or less impossible to bend any individual demand into these wires. i.e. to bend the known wires in such a way that the individual requirements are fulfilled. Therefore they are useful only for a very short treatment period or for some abnormal situations.

In addition the span, the distance from tooth to tooth, has a very small biological variability. This means that even if the elasticity of a wire may be extremely high, every elastic wire with a cross-section of 0.016×0.022, 0.017×0.022, 0.018×0.022 or even 0.016×0.016 inches, which are the common wire sizes, in a slot of 0.018×0.022 inches separated by a span of approximately 4 to 6 mm (0.16 to 0.24 inches) will still cause enormous forces. These forces which are directly influenced by the physical requirements of the size of the wire and the span are not sufficiently controllable or adjustable and are not within biological limits.

In numerous articles damage and problems with too high forces are described. They range from root resorptions, damage to the parodontium, necrosis by lack of blood supply and resulting loss of tooth movements (ankylosis), up to the failure of handling a case because too high a force moment very often does not cause the required intrusion in the front but rather an extrusion of the molars by bigger rotation moments or torques for example. A mismanagement in this way may cause temporomandibular joint problems and muscle diseases with headache. The generally accepted biological demands in this field are e.g. described in the articles of Kaare Reitan, D.D.S., U.S.D., Ph.D., e.g. in the treatise "Biomechanische Prinzipien der Gewebsreaktion" in "Grundlagen und moderne Techniken der Kieferorthopädie", pages 149 to 279, and by other scientists.

A summary of these ideas is to be found in the book "Current Principles and Techniques" by T. M. Graber/B. F. Swain.

The required forces should work simultaneously in three dimensions, be controllable as to the wanted direction and amount of movement and cause less damage to biological tissue. This cannot be achieved in the common systems, even not by means of the more elastic wire alloys discussed above. While round wires with smaller diameters, which consequently cause weaker forces, are available, these round wires do not work three-dimensionally and are thus useful only for the initial levelling period.

SUMMARY OF THE INVENTION

Thus the object of this invention is to provide a system of treatment and an orthodontic method which introduce the advantages of functional treatment philosophies like low inductive and adaptable forces into fixed appliance treatment techniques and avoid the disadvantages of both techniques.

This object is achieved by the invention.

The idea underlying the present invention is to use a controlled and low amount of applied force by using smaller rectangular wires with high flexibility in the bracket slot. According to the invention, the short edges of the wires are shorter than 0.018 inches and the long edges are shorter than 0.022 inches.

The rectangular archwires according to the invention have the following essential advantages vis-à-vis the conventional thicker wires:

The patient realizes considerably less pain.

The wires according to the invention are effective for a considerably longer period of time, as due to their small cross-section they have more play in the slot of the brackets or bands.

They act like springs although they have the shape of a straight wire, so they are suitable for all treatment periods and for all relations of teeth positions. As they act like springs and as their shape is more or less a straight unbroken wire just from the beginning, a very accurate and quick treatment is possible. When using a stainless steel alloy or similar alloys for the wires according to the invention individual gables and angulations are possible.

Multiloop arches with a rectangular shape, low cross-sections and a high flexibility in the slots are also possible with the wires according to the invention and are highly effective.

The wires according to the invention provide better elasticity since the elasticity of a wire is increasing proportionally by reducing the cross-section inbetween a distinct and predetermined distance. According to the invention, a displacement of the axial inclination of an individual tooth can be provided individually and more precisely by the orthondotist via a torison of the wire. Such a torque cannot be provided by wires made of the more elastic alloys mentioned above, irrespective of their sizes.

Summing up, a very individual treatment in relation to anomaly and biology and a reduction in treatment time is possible with the wires according to the invention because movements of teeth start just from the very beginning in the right direction in all three dimensions, supported by biological forces, and damage and pain are reduced.

Contrary to the archwires conventionally used, which usually must act with too strong forces for a short time period with less blood supply or even loss of blood supply, the system of this invention avoids these problems and makes it possible to apply forces for a longer period of time and to keep them biologically acceptable.

The three-dimensional impulse caused by the wire works as a guide for the root movement, e.g. as a "flowing" of the roots in the spongeous alveolar bed so that the individual control which is necessary for each patient is guaranteed. The apex of the roots does not grind at the compact continually which is often the case in conventional techniques, as in the system according to the invention the roots have the possibility by means of the impulses and by means of a great range of freedom in space to go back into the soft part of the spongiosa of the alveolar bone.

The handling according to the invention reduces root resorptions of the teeth by a very high percentage and causes additionally much quicker movement of the teeth with a reduction of treatment time.

The reduction of forces causes a much better handling of movement directions especially in handling extrusions and intrusions of anterior or posterior teeth, which is essential in handling e.g. open bites.

With the present invention cases can be handled successfully in which conventional treatment would fail or in which the treatment time would be much longer than necessary, and root resorptions are avoided.

As the blood supply is not squeezed off or affected with the system according to the invention, bone remodelling activities are much quicker, necroses and root resorptions land parodontal damage can be avoided or considerably reduced.

In summary, when using the wires according to the invention it is possible to achieve treatment results faster, more easily and better, causing less pain and damage to the patient than with the conventional system.

The wires according to the invention can be made from any material, especially any alloys conventionally used for archwires.

According to another aspect of the invention, the dimensions of the slot receiving the archwire in the bracket or band are suitably selected with respect to the dimensions of the wire, thus allowing a finer adjustability in particular for the final phase of the treatment. For the sake of convenience, in the following the term "bracket" is used, it should, however, be noted that this term when used in this specification comprises both brackets and bands.

The brackets according to the invention comprise rectangular slots the short sides of which are shorter than 0.018 inch and the long sides of which are shorter than 0.022 inch.

According to yet another aspect of the invention a system of treatment for use in orthodontic methods comprises at least one rectangular archwire wherein the two shorter edges of the wire are shorter than 0.016 inches and the two longer edges of the wire are shorter than 0.022 inches, and at least one bracket or band having a rectangular slot for receiving said archwire wherein the shorter sides of the cross-section of the slot are shorter than 0.018 inches and the longer sides of the cross-section are shorter than 0.022 inches.

According to yet another aspect of the invention an orthodontic method for the treatment of faulty positions of teeth is provided. In this-method at least one archwire having a cross-section of less than 0.016×0.022 inches and at least one bracket with a rectangular slot having a cross-section of less than 0.018×0.022 inches is used.

The system of treatment according to the invention and the orthodontic method according to the invention can be described by the term "functional orthodontics", since they combine the advantages of the above described functional dental orthopedics, which uses intermittent functional treatment by means of removable appliances, with the advantages of orthodontics, which uses a more mechanical way of influence on the teeth. In accordance with the invention selective controlled forces are used which can be obtained neither by the known small round archwires alone nor by the known stiff rectangular archwires. With the system of treatment according to the invention intermittently acting forces can be applied, which so far were observed only in functional dental orthopedics. In contrast to functional dental orthopedics, in the system of the invention intermittent forces may also be applied three-dimensionally, whereby a selective three-dimensional tooth movement is made possible. In connection with the clearly reduced forces, the system of the invention provides a link between traditional orthodontics and functional therapy. By a suitable choice of the archwire cross-section and adjustment of the crosssections of the wires and corresponding slots in such a way that the wires have sufficient play in the slots, in particular by the intermittently applied impulses of force, a more gentle, speedy and selective treatment of the patient is made possible.

In contrast to the conventional treatment concepts with fixed appliances which follow the demand for "full engagement philosophy" of wire and slot, the functional orthodontic treatment method according to the invention provides freedom of movement of the wire in the slot to a high extent. Thus the functional orthodontic treatment method according to the invention relates to the biological demands and makes it possible to handle them. The present invention provides both new wires and new brackets or bands as well as a new way of interaction between wires and brackets.

Since, according to the invention, the applied forces are different from conventional systems in terms of their impulse, magnitude and type, the biological reactions are different. This is comparable to the case of different chemical compounds which also cause different reactions of the human body.

DESCRIPTION OF THE PREFERRED EMBODIMENTS

According to the present invention, the archwires preferably have cross-sections of 0.009×0.018, 0.010×0.018, 0.011×0.018, 0.012×0.018, 0.013×0.018, 0.014×0.018, 0.015×0.018 inches or 0.009×0.020, 0.010×0.020, 0.011×0.020, 0.012×0.020, 0.013×0.020, 0.014×0.020 and 0.015×0.020 inches or 0.010×0.022, 0.011×0.022, 0.012×0.022, 0.013×0.022, 0.014×0.022 and 0.015×0.022 inches. Any intermediate sizes are also within the scope of the invention, like e.g. wires with long edges of 0.019 inches or 0.021 inches, in combination with the above mentioned sizes of the short edges. It is also within the scope of the present invention to have archwires in which the shorter edge of their cross-section is shorter than 0.009 inch, namely 0.005 inch, 0.006 inch, 0.007 inch or 0.008 inch, for specific purposes. The long edge of these archwires is preferably 0.020 inch or less. Wires with a thickness of 0.016×0.020 or 0.016×0.022 inches may be used as final archwires.

It has been found that for example a rectangular heat-treated stainless steel wire having a cross-section of 0.010× 0.020 inches has all desired characteristics such as hardness, bending strength and resilience and thus the optimum force required for bending. During bending such a wire can be drawn optimally through the so-called "bending finger". For example, a wire with a thickness of 0.010×0.020 inches has a cross-section which is more than 40% smaller than the cross-section of conventional wires having a thickness of 0.016×0.022 inches and thus has a correspondingly reduced bending strength and force required for bending. Wires with a thickness of 0.010×0.022, 0.011×0.022 and 0.012×0.022 inches or 0.010×0.020, 0.011×0.020 and 0.012×0.022 inches can be used e.g. for the controlled intrusion of the front teeth (incision). At the same time they allow good bucco-lingual control of the molars with simultaneous easy levelling processes. For this purpose, wires with an even smaller cross-section having a shorter edge of 0.005 to 0.009 inch may be used. Wires with a thickness of 0.014×0.022 and 0.015×0.022 inches or 0.014×0.020 and 0.015×0.020 inches may for example be used as level arches with torque control and as working arches, such as final and ideal arches.

Essentially all conventional archwire alloys may be used as wire material, such as those traded by Ormco Corporation, Glendora, Calif., U.S.A., cf. their brochure "The right wire for every phase of treatment", Print No. 070-5011, 1987.

Preferably stainless steel wires are used, which are heat-treated, e.g. by means of a flame, after bending. By this heat-treatment an additional resilience can be obtained.

The preferred size of the slot in the brackets is 0.016× 0.022 or 0.017×0.022 inches.

With thin wires, slots having a cross-section of 0.017× 0.020 inches, 0.017×0.019 inches, 0.016×0.020 inches and 0.016×0.019 inches may also be used. Wires having short edges being shorter than 0.010 inch are preferably used in connection with slots having short sides with a length of 0.016 inch or less.

A wire with a cross-section of 0.010×0.020 inches in a slot having a cross-section with a short side of 0.016 or 0.017 inches and a long side of 0.020 to 0.022 inches has enough play to allow a controlled biologically acceptable three-dimensional force. According to the invention, the play of the wire in the slot in the direction of the short edge can be at least 0.003 inches and up to 0.012 inches, preferably up to 0.007 inches, whereas in conventional systems with wires of 0.016×0.022 inches and slots of 0.018×0.022 inches it is only up to a maximum of 0.002 inches.

The slots which are smaller vis-à-vis conventional techniques moreover have the advantage that the bracket is flatter and thus more pleasant for the lip or cheek of the patient.

Besides the sizes of the archwires and slots explicitly mentioned above, wires and slots of any intermediate sizes are also within the scope of the invention and the sizes need not be in steps of one thousandth of an inch.

In a system of treatment consisting of the above described wires and brackets, the angulations of the above described conventional techniques are also adjustable.

In conventional systems, the bracket is firmly connected to its base. In the system of treatment according to the invention, the bracket may also be firmly fixed on its base, e.g. welded or soldered to the base. Alternatively, in a preferred embodiment of the invention the bracket may be slidably mounted on its base. When the bracket is slidably mounted, it has the advantage that the brackets may be exchanged any time and even in partial sections and the cross-sections of the slots may be adapted to the respective treatment situation without the need to remove the base of the brackets, and without damaging the teeth by a new conditioning and glue phase. Moreover, by means of the slidable mounting of the bracket onto its base, the duration of the treatment is considerably shortened and thus the costs reduced.

In view of the fact that brackets with different slot thicknesses and slot cross-sections can be quickly and easily exchanged with each other, the orthodontist is given a large variety of possible applications of smaller, intermittently acting forces in the initial phase of the treatment, and for the final phase of the treatment the orthodontist may for example use a full engagement technique with a thinner archwire due to the reduction of the cross-sections of the slots according to the invention.

It is particularly advantageous when the adjustment of the slidable bracket on the base can be varied in its height and rotation as well as its tilt. It is thus possible to correct positioning errors of the bracket base on the tooth by a suitable shift of the slidable bracket on its base. Thus, treatment errors can be eliminated or at least corrected.

The vertically and rotatably adjustable mounting of the bracket on its base can be carried out in practice in any way known to the person skilled in the art.

In the following a typical treatment example will be described in order to demonstrate the practical value of the invention.

EXAMPLE

The case described in the Example includes basically all difficulties that can be involved in orthodontic treatment.

The patient is an adult patient without any support of growth and with reduced biological reactions.
There are severe sceletal deformities with a tendency of crossbite on the right side, a severe open bite up to the molars, and a severe overjet.
There are severe dental deformities with rotations, angulations, asymmetrical missing teeth and periodontal diseases in an already progressive situation. There is loss of bone between the teeth Nos. 16 and 14.
There are severe intermaxillary relations concerning overbite, overjet, midline shifting and asymmetric anchorage situations for treatment appliances.
The tooth No. 38, i.e. the lower left wisdom tooth, is misaligned.
The patient does not accept any surgical sceletal correction, so that only orthodontic treatment methods can be applied.
At the beginning of the treatment, because of midline shifting and because of the bad angulated lower right canine, the tooth No. 44 (i.e. the first lower right premolar) is extracted.

As treatment appliances, a palatal bar according to Goshgarian and a so-called HG were used.

The Goshgarian is tightened in the upper jaw along the palate from tooth No. 16 to tooth No. 26. The HG (headgear) comprises two elements, namely the facebow and the neckstrap or headstrap. The neckstrap is attached to the facebow and causes the molars to be anchored or tilted or physically or tiltingly distalized or vertically retained. In the present case, all torques are used in varying degrees.

The treatment appliances are applied so that there is full bending in the upper and lower jaw.

As orthodontic wires, stainless steel wires with a size of 0.010×0.022 inches, 0.012×0.022 inches and 0.014×0.022 inches are used. The active treatment time with braces is two years, and the retention time is ten months.

The treatment provides the following results.

The crossbite can be handled without further bite opening.
The overbite and overjet can be corrected.
Angulations and rotations can be corrected as well.
The spaces of missing teeth can be closed.
The impacted tooth No. 38, i.e. the lower left wisdom tooth, can be aligned.
The periodontal diseases can be stopped in progress.
The bimaxillary protruded profile can be reduced to normal aesthetics.
The stability of the treatment results can be guaranteed due to the 10-month retention time after active treatment.

In the lower front some root resorptions are still to be seen. However, these are acceptable because of the severeness of the problems and difficulties involved in the present case, because of the amount of movements, because of the adult age of the patient, because of missing growth, and because of the prerequisite that only orthodontic treatment, but no sceletal surgery, is accepted by the patient.

The present case demonstrates the advantages provided by the present invention. With conventional techniques the present case could not have been treated with comparable success. It is to be expected that with conventional treatment extreme root resorptions in the upper and the lower jaw would have occurred, without that the front open bite could have approximated closing.

I claim:

1. Apparatus comprising at least one orthodontic wire for use as an archwire and at least one bracket, said at least one wire having a rectangular cross-section and having two short edges and two long edges, said short edges being not longer than 0.015 inches (0.381 mm) and said long edges being not longer than 0.020 inches (0.508 mm), said at least one bracket having a single rectangular cross-section slot, said slot having two short sides and two long sides, the short sides being 0.018 inches (0.457 mm) and the long sides being 0.022 inches (0.559 mm), the dimensions of said at least one wire and said slot being selected so that, when said at least one wire is inserted into said slot, there is play of the wire in the slot.

2. Apparatus comprising at least one orthodontic wire for use as an archwire and at least one bracket, said at least one wire having a rectangular cross-section and having two short edges and two long edges, said short edges being not longer than 0.015 inches (0.381 mm) and said long edges being not longer than 0.020 inches (0.508 mm), said bracket having a single rectangular cross-section slot, said slot having two short sides and two long sides, the short sides being smaller than 0.018 inches (0.457 mm) and the long sides being smaller than 0.022 inches (0.559 mm), the dimensions of said at least one wire and said slot being selected so that when said at least one wire is inserted into said slot, the short edges of the wire are at least 0.003 inches (0.076mm) shorter than the short sides of the slot so that there is play of the at least one wire in the slot in the direction of the short edge.

3. Apparatus according to claim 1 or 2, wherein the two short edges of said at least one wire have a length of 0.005 inches (0.127 mm) to 0.015 inches (0.381 mm).

4. Apparatus according to claim 3, wherein the two short edges of said at least one wire have a length of 0.010 inches (0.254 mm) to 0.015 inches (0.381 mm).

5. Apparatus according to claim 1 or 2, wherein the at least one wire is made of heat-treated steel or is heat-treated after having been brought into its desired shape.

6. Apparatus according to claim 1 or 2, wherein the at least one wire consists of an alloy conventionally used for orthodontic wires.

7. Apparatus according to claim 1 or 2, wherein the shorter sides of the slot have a length of 0.016 inches (0.406 mm).

8. Apparatus according to claim 1 or 2, wherein the longer sides of the slot have a length of 0.019 inches (0.482 mm).

9. An apparatus according to claim 1 or 2, further comprising a plurality of said orthodontic wires and brackets in the form of a set.

10. Apparatus according to claim 9, wherein the brackets each comprise a base and are slidably arranged thereon.

11. Apparatus according to claim 1 or 2, wherein the shorter sides of the slot have a length of 0.017 inches (0.432 mm).

12. Apparatus according to claim 1 or 2, wherein the longer sides of the slot have a length of 0.020 inches (0.508 mm).

13. A method of using orthodontic wire with a dental bracket having a single rectangular cross-section slot, having a slot cross-section of 0.018×0.022 inches (0.457×0.559 mm) said wire having a rectangular cross-section and two short edges and two long edges, the short edges being not longer than 0.015 inches (0.381 mm) and the two long edges being not longer than 0.020 inches (0.508 mm), which comprises selecting the wire and the bracket so that there is play of the wire in the slot and inserting said wire into said slot of said dental bracket.

14. A method of using orthodontic wire with a dental bracket having a single rectangular cross-section slot, said wire having a rectangular cross-section and having two short edges and two long edges, the short edges being not longer than 0.015 inches (0.381 mm) and the two long edges being not longer than 0.020 inches (0.508 mm), which comprises selecting the wire and the bracket so that there is play of the wire in the slot in the direction of the short edge of at least 0.003 inches (0.076mm) and inserting said wire into said slot of said dental bracket, said bracket having a slot cross-section of 0.018×0.022 inches (0.457×0.559 mm).

15. A method for the orthodontic treatment of faulty positions of teeth with orthodontic wire having a rectangular cross-section having two short edges and two long edges and orthodontic brackets each having a slot receiving said wire, which comprises selecting the dimensions of the orthodontic wire to be used as an archwire so that there is play of the wire in the slots of the brackets throughout all phases of treatment in such a way that three-dimensional tooth movement with biologically acceptable forces can be selectively achieved.

16. A method according to claim 15, wherein the forces during treatment are applied intermittently by means of the archwire, the archwire having a rectangular cross-section of not longer than 0.015×0.020 inches (0.381 mm×0.508 mm).

* * * * *

UNITED STATES PATENT AND TRADEMARK OFFICE
CERTIFICATE OF CORRECTION

PATENT NO. : 5,588,833
DATED : December 31, 1996
INVENTOR(S) : Georg Risse

It is certified that error appears in the above-indentified patent and that said Letters Patent is hereby corrected as shown below:

Title page, item [30] Foreign Application Priority data insert--
June 26, 1990  [DE]  Germany  4020315.8--

Signed and Sealed this

Twenty-ninth Day of July, 1997

Attest:

BRUCE LEHMAN

Attesting Officer

Commissioner of Patents and Trademarks